(12) United States Patent
Yamagawa et al.

(10) Patent No.: US 10,813,850 B2
(45) Date of Patent: Oct. 27, 2020

(54) DENTAL RESIN COMPOSITE MATERIAL, METHOD OF PRODUCING DENTAL RESIN COMPOSITE MATERIAL, AND POLYARYLETHERKETONE RESIN FOR PRODUCING DENTAL RESIN COMPOSITE MATERIAL

(71) Applicant: TOKUYAMA DENTAL CORPORATION, Tokyo (JP)

(72) Inventors: Junichiro Yamagawa, Tokyo (JP); Tomonao Shimizu, Tokyo (JP); Yuko Nagasawa, Tokyo (JP); Anna Uehara, Tokyo (JP)

(73) Assignee: TOKUYAMA DENTAL CORPORATION (JP)

( * ) Notice: Subject to any disclaimer, the term of this patent is extended or adjusted under 35 U.S.C. 154(b) by 0 days.

(21) Appl. No.: 16/335,069

(22) PCT Filed: Oct. 12, 2017

(86) PCT No.: PCT/JP2017/037072
§ 371 (c)(1),
(2) Date: Mar. 20, 2019

(87) PCT Pub. No.: WO2018/070495
PCT Pub. Date: Apr. 19, 2018

(65) Prior Publication Data
US 2019/0274931 A1    Sep. 12, 2019

(30) Foreign Application Priority Data

Oct. 13, 2016  (JP) ................................. 2016-202095

(51) Int. Cl.
*A61K 6/891* (2020.01)
*A61K 6/84* (2020.01)
*A61K 6/831* (2020.01)

(52) U.S. Cl.
CPC .............. *A61K 6/891* (2020.01); *A61K 6/831* (2020.01); *A61K 6/84* (2020.01)

(58) Field of Classification Search
None
See application file for complete search history.

(56) References Cited

U.S. PATENT DOCUMENTS

| 2011/0178237 A1* | 7/2011 | Ono ....................... C08G 65/46 524/592 |
| 2014/0364533 A1* | 12/2014 | Yamagawa .............. C08K 9/06 523/115 |
| 2019/0274931 A1* | 9/2019 | Yamagawa ............. A61K 6/827 |

FOREIGN PATENT DOCUMENTS

| JP | H10-501828 A | 2/1998 |
| JP | 2004-526859 A | 9/2004 |
| JP | 2012-171981 A | 9/2012 |
| JP | 2012-236981 A | 12/2012 |
| JP | 2013-144783 A | 7/2013 |
| JP | 2014-152150 A | 8/2014 |
| JP | 2014152150 A * | 8/2014 |
| JP | 2014-201673 A | 10/2014 |
| WO | WO-95-34594 A1 | 12/1995 |
| WO | 02/096974 A2 | 12/2002 |
| WO | WO-2009-057255 A1 | 5/2009 |

OTHER PUBLICATIONS

Vestalee PEEK, Biomaterials for implant applications. Evonik (Year: 2020).*
Japanese Office Action for Application No. 2018-545061 dated Jan. 7, 2020 with English translation (6 pages).
Japanese Office Action for Patent Application No. JP 2018-545061 dated Jun. 30, 2020 (8 pages). JP2012171981A Abs only.

* cited by examiner

*Primary Examiner* — Peter A Salamon
(74) *Attorney, Agent, or Firm* — Harness, Dickey & Pierce, P.L.C.

(57) ABSTRACT

A dental resin composite material is provided that is reduced in darkness of its color tone, and also reduced in burning and color unevenness. Specifically provided are a dental resin composite material including 100 parts by mass of a polyaryletherketone resin, 10 parts by mass to 300 parts by mass of inorganic particles, and 90 ppm or less of an impurity having an aromatic ring, a method of producing the dental resin composite material, and a polyaryletherketone resin for producing a dental resin composite material, to be used for producing the dental resin composite material.

6 Claims, No Drawings

DENTAL RESIN COMPOSITE MATERIAL, METHOD OF PRODUCING DENTAL RESIN COMPOSITE MATERIAL, AND POLYARYLETHERKETONE RESIN FOR PRODUCING DENTAL RESIN COMPOSITE MATERIAL

CROSS-REFERENCE TO RELATED APPLICATIONS

This application is a U.S. National Stage Application of International Application No. PCT/JP2017/037072, filed on Oct. 12, 2017, and published in Japanese as WO 2018/070495 A1 on Apr. 19, 2018 and claims priority to Japanese Application No. 2016-202095, filed on Oct. 13, 2016. The entire disclosures of the above applications are expressly incorporated herein by reference.

BACKGROUND

Technical Field

The present invention relates to a dental resin composite material, a method of producing a dental resin composite material, and a polyaryletherketone resin for producing a dental resin composite material.

Related Art

A polyaryletherketone resin, such as polyetheretherketone or polyetherketoneketone, is used in the field of dentistry. The polyaryletherketone resin to be used as a dental material is often used in a form of a resin composite material obtained by blending the polyaryletherketone resin with inorganic particles in order to, for example, improve a mechanical strength or adjust a color tone (JP 2013-144783 A or JP 2014-152150 A). In addition, the polyaryletherketone resin has a beige to dark brown color tone. Therefore, when the polyaryletherketone resin is used as a dental material, in order to ameliorate an appearance of the dental material placed in an oral cavity, the color tone is often adjusted by, for example, adding an inorganic pigment, such as titania, as the inorganic particles to the polyaryletherketone resin.

However, as a result of an investigation made by the inventors of the present invention into the related-art dental resin composite material obtained by blending a polyaryletherketone resin with inorganic particles, it has been found that even when the inorganic pigment are blended into the dental resin composite material in order to ameliorate the appearance of the dental resin composite material placed in an oral cavity, the dental resin composite material may exhibit an appearance unsuitable as a dental material, that is, dullish darkness, or have burning or color unevenness.

The present invention has been made in view of the above-mentioned circumstances, and an object of the present invention is to provide a dental resin composite material reduced in darkness of its color tone, and also reduced in burning and color unevenness, a method of producing the dental resin composite material, and a polyaryletherketone resin for producing the dental resin composite material.

SUMMARY

The above-mentioned object is achieved by embodiments of the present invention to be described below.

That is, according to one embodiment of the present invention, there is provided a dental resin composite material, including: 100 parts by mass of a polyaryletherketone resin; 10 parts by mass to 300 parts by mass of inorganic particles; and 90 ppm or less of an impurity having an aromatic ring.

According to another embodiment of the present invention, there is provided a method of producing a dental resin composite material, including a step of mixing 100 parts by mass of a polyaryletherketone resin (A) containing 150 ppm or less of an impurity having an aromatic ring and 10 parts by mass to 300 parts by mass of inorganic particles in a molten state.

In the method of producing a dental resin composite material according to the embodiment of the present invention, it is preferred that the polyaryletherketone resin (A) containing 150 ppm or less of an impurity having an aromatic ring be produced at least through a step of subjecting polyaryletherketone resin powder (B) containing the impurity having an aromatic ring to heating treatment in a temperature range of from a glass transition temperature of the polyaryletherketone resin powder (B) or more to less than a melting point of the polyaryletherketone resin powder (B) in a heat treatment apparatus while replacing a gas in the heat treatment apparatus.

According to still another embodiment of the present invention, there is provided a polyaryletherketone resin for producing a dental resin composite material, to be used for producing the dental resin composite material according to the embodiment of the present invention, the polyaryletherketone resin for producing a dental resin composite material including 150 ppm or less of an impurity having an aromatic ring.

Advantageous Effects of Invention

As described above, according to the present invention, the dental resin composite material reduced in darkness of its color tone, and also reduced in burning and color unevenness, the method of producing the dental resin composite material, and the polyaryletherketone resin for producing the dental resin composite material can be provided.

DETAILED DESCRIPTION

A dental resin composite material according to an embodiment of the present invention includes: 100 parts by mass of a polyaryletherketone resin; 10 parts by mass to 300 parts by mass of inorganic particles; and 90 ppm or less of an impurity having an aromatic ring.

In the dental resin composite material according to this embodiment, the content of the impurity having an aromatic ring is 90 ppm or less. Accordingly, the dental resin composite material according to this embodiment is more easily reduced in darkness of its color tone, and reduced in burning and color unevenness.

In investigating the dental resin composite material according to this embodiment, the inventors of the present invention have investigated the reason why a related-art dental resin composite material exhibits an appearance and color tone unsuitable as a dental material, that is, dullish darkness, or has burning or color unevenness.

First, there are many possible factors influencing the appearance of the dental resin composite material, and examples thereof include: a material itself for a main component to be used for the dental resin composite material; the combination of the polyaryletherketone resin and the inorganic particles included in the dental resin composite material; the degree of uniformity-nonuniformity of a resin matrix forming the dental resin composite material; impurities resulting from various raw materials to be used for producing the dental resin composite material; natural oxidation of the surface of the dental resin composite material or its surface alteration resulting from, for example, a chemical solution at the time of washing; adhesion of a contaminant, such as contamination; surface alteration during machining processing of the dental resin composite material into a desired shape suitable for dental treatment; a material for a mold surface, and the presence or absence of a mold release agent thereon and the kind thereof in the molding of the dental resin composite material into a desired shape suitable for dental treatment; pressure/heat in the production steps of the dental resin composite material; and the degree of light scattering resulting from surface unevenness of the surface of the dental resin composite material.

The inventors of the present invention have investigated not only those many factors, but also synergistic influences of combinations of two or more factors selected from those many factors. As a result, the inventors of the present invention have presumed that the appearance failure of the related-art dental resin composite material is due to causes described below.

First, (a) the darkness of the color tone is considered to result from the fact that the optical effect of an inorganic pigment having high whiteness to be used as the inorganic particles is not sufficiently exhibited in the dental resin composite material owing to low transparency of the polyaryletherketone resin. (b) In addition, the burning and color unevenness are considered to result from heating or pressure in a step of melt-mixing the polyaryletherketone resin and the inorganic particles to form a composite, or molding the melt mixture. Besides, in each of the cases (a) and (b), it is considered that the presence of a certain impurity contained in the dental resin composite material has a synergistic influence. That is, when the certain impurity is present in a large amount in the matrix or melt mixture of the dental resin composite material, it is considered that the transparency of the polyaryletherketone resin is liable to be lowered, or heat or pressure acts on the certain impurity to significantly influence the color tone of the dental resin composite material.

Meanwhile, as the impurity, one derived from the polyaryletherketone resin, and one derived from the inorganic particles are mainly conceivable. In addition, the inorganic particles to be used for the dental resin composite material are often subjected to surface treatment with a hydrophobizing agent, such as a silane coupling agent. Therefore, in the dental resin composite material using the inorganic particles subjected to surface treatment with the hydrophobizing agent, the hydrophobizing agent is also considered as one of the supply sources of impurities. In addition, an external environment, such as a melt-kneading apparatus to be used in the process of production of the dental resin composite material, is also considered as a supply source of an impurity. However, in consideration of the potential to be a supply source of a large amount of an impurity, and the potential to be a supply source of an organic impurity susceptible to the influence of heat or pressure, it is presumed that the supply source of the impurity that is most liable to influence the color tone out of the above-mentioned supply sources of impurities is the polyaryletherketone resin.

Therefore, the inventors of the present invention have considered that, when the content of the impurity having an aromatic ring presumed to be mainly derived from the polyaryletherketone resin in the dental resin composite material can be reduced, the appearance failure of the dental resin composite material can be ameliorated, and have found the dental resin composite material according to this embodiment. The details of each constituent component of the dental resin composite material according to this embodiment are described below.

Polyaryletherketone Resin

The polyaryletherketone resin is a thermoplastic resin containing, in a structural unit thereof, at least an aromatic group, an ether group (ether linkage), and a ketone group (ketone linkage), and often having a linear polymer structure in which benzene rings (phenylene groups) are bonded through the ether group and the ketone group. Typical examples of the polyaryletherketone resin include polyetherketone (PEK), polyetheretherketone (PEEK), polyetherketoneketone (PEKK), and polyetherketoneetherketoneketone (PEKEKK). The structural formula of the polyetheretherketone is shown below.

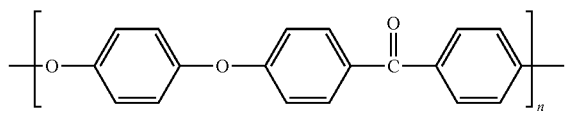

The aromatic group contained in the structural unit of the polyaryletherketone resin may have a structure having two or more benzene rings, such as a biphenyl structure. In addition, the structural unit of the polyaryletherketone resin may contain a sulfonyl group or any other copolymerizable monomer unit.

From the viewpoints of the color tone and physical properties, the polyaryletherketone resin to be used in the dental resin composite material according to this embodiment is preferably polyetheretherketone having a repeating unit in which the ether group and the ketone group contained in the main chain are arranged in the order "ether-ether-ketone". The polyetheretherketone having the repeating unit is commercially available under, for example, the product name "PEEK", and specific examples thereof include VESTAKEEP (trademark, Daicel-Evonik Ltd.) and VICTREX (trademark, Victrex plc).

Impurity Having Aromatic Group

The dental resin composite material according to this embodiment contains an impurity having an aromatic group. The impurity having an aromatic group is contained in a polyaryletherketone resin (hereinafter sometimes referred to as "raw material resin") to be used as a raw material for producing a dental resin composite material, and specifically refers to a compound having an aromatic ring to be measured by a measurement method to be described later, among starting raw material substances, a reaction solvent, a catalyst, an additive, a byproduct, and a decomposition product, used or produced in a step of synthesizing the polyaryletherketone resin and a subsequent step. Specific examples of the impurity having an aromatic group include: (i) hydroquinone, difluorobenzophenone, dihydroxybenzophenone, diphenyl ether, benzophenone, diphenyl sulfone, diphenyl sulfide, phenol, biphenyl, fluorohydroxybenzophenone, difluorochalcone, diphenoxybenzene, benzophenone dicarboxylic acid, dibenzofuran, and naphthalene; (ii) isomers of the compounds exemplified in (i); and (iii) derivatives, such as alkyl group- or halogen group-substituted products, of the compounds exemplified in (i) and (ii). The derivatives of difluorobenzophenone, dihydroxybenzophenone, diphenyl sulfone, phenol, fluorohydroxybenzophenone, fluorohydroxybenzophenone, difluorochalcone, diphenoxybenzene, benzophenone dicarboxylic acid, and dibenzofuran are each particularly frequently detected as the impurity having an aromatic group. The impurity having an aromatic group has a sufficiently small molecular weight as compared to the molecular weight of the polyaryletherketone resin. A specific molecular weight is not particularly limited, but is generally less than 2,000 and is less than 1,000 in most cases.

The content of the impurity having an aromatic ring in the dental resin composite material according to this embodiment is 90 ppm or less, more preferably 50 ppm or less, still more preferably 18 ppm or less, particularly preferably 2 ppm or less, most preferably below the detection limit in measurement (0 ppm). The impurity having an aromatic ring is generally contained in a dental resin composite material, and hence the "content of the impurity having an aromatic ring" in this case means the total content of all kinds of impurities each having an aromatic ring in the dental resin composite material. The same applies to the raw material resin. When the content of the impurity having an aromatic ring in the dental resin composite material is 90 ppm or less, a dental resin composite material excellent in color tone and appearance is obtained.

In addition, the content of the impurity having an aromatic ring in the polyaryletherketone resin (raw material resin) for producing a dental resin composite material, to be used for producing the dental resin composite material according to this embodiment, is preferably 150 ppm or less, more preferably 100 ppm or less, still more preferably 30 ppm or less, particularly preferably 3 ppm or less, most preferably below the detection limit in measurement (0 ppm). When the dental resin composite material is produced using the raw material resin in which the content of the impurity having an aromatic ring is 150 ppm or less, the content of the impurity having an aromatic ring in the dental resin composite material can be easily reduced to ppm or less. Accordingly, as a result, a dental resin composite material excellent in color tone and appearance is obtained. However, in consideration of the fact that the content of the impurity having an aromatic ring is also reduced during melt-mixing using the raw material resin and the inorganic particles, the content of the impurity having an aromatic ring in the raw material resin may be more than 90 ppm and 150 ppm or less.

The measurement of the content of the impurity having an aromatic ring in each of the dental resin composite material according to this embodiment and the raw material resin to be used for production thereof is performed using a gas chromatograph with a thermal desorption apparatus. A volatile component generated by heating a sample in the thermal desorption apparatus is separated using the gas chromatograph apparatus directly connected to the thermal desorption apparatus, and is quantified and identified. Mass spectrometry to be performed by analyzing a mass spectrum is used for the identification of the volatile component. A heating temperature in the thermal desorption apparatus is set to a temperature higher than the melting point of the polyaryletherketone resin included in the dental resin composite material by 60° C. (±5° C.), and the sample is heated for a holding time of 10 minutes. A temperature at an interface between the thermal desorption apparatus and the gas chromatograph is from 280° C. to 300° C. The gas chromatograph uses a helium gas as a carrier gas, and has a gas flow rate of 1.0 mL/min. The temperature program of a column oven is set to an initial temperature of 40° C., a temperature increase rate of 20° C./min, and a final temperature of 350° C. (giving a retention time of 15.5 minutes). The total content of compounds each having an aromatic ring that appeared as peaks during a period in which the temperature of the gas chromatograph starting at 40° C. reached 350° C. was determined as the content of the impurity having an aromatic ring. As a column, a column having a length of 30 m, an inner diameter of 0.25 mm, a stationary phase liquid of 5% diphenyl-95% dimethylpolysiloxane, and a film thickness of 0.25 μm is used. A GC-IF temperature is 250° C. A mass spectrometer is specified in JIS K0123, and the mass spectrometer employs an Electron Ionization (EI) method as an ionization method and has an ion source temperature of 250° C., an ionization energy of 70 eV, and a mass-to-charge ratio scanning range of from 50 to 600.

A measurement procedure is as described below. A predetermined amount of the dental resin composite material or the raw material resin is measured out as a sample in a sample holder, and the sample holder is introduced into the thermal desorption apparatus. When the sample measures more than 2 mm on a side, the sample is cut or pulverized to 2 mm or less before being placed in the sample holder. The thermal desorption temperature of the thermal desorption apparatus is set to a temperature higher than the melting point of the polyaryletherketone resin contained in the sample by +60° C. (±5° C.), and the sample is held for 10 minutes. After that, a first measurement is initiated, and the resultant chromatogram and mass spectrum are used to perform quantification and identification. The sample holder in the state of having placed therein the sample used for the first measurement is used as it is to perform a second measurement. The second measurement is performed under the same temperature and time conditions as the first measurement.

Now, when the measured value of the amount of the impurity having an aromatic ring measured in the second measurement is less than 5% of the measured value of the amount of the impurity having an aromatic ring measured in the first measurement, measurement is ended, and a value obtained by summing up the measured value in the first measurement and the measured value in the second measurement is defined as the "content of the impurity having an aromatic ring." Meanwhile, when the measured value of the amount of the impurity having an aromatic ring measured in the second measurement is 5% or more of the measured value of the amount of the impurity having an aromatic ring measured in the first measurement, a third measurement is performed under the same conditions as the first measurement. Similarly, measurement is repeated until the measured value of an (n+1)-th measurement becomes less than 5% of an n-th measured value. Then, when the measured value of the (n+1)-th measurement becomes less than 5% of the n-th measured value, measurement is terminated, and a value obtained by summing up the first measured value to the (n+1)-th measured value is defined as the "content of the impurity having an aromatic ring." The quantification of each kind of impurity having an aromatic ring is performed by an external standard method based on a calibration curve using diphenyl sulfone as a standard substance.

<Inorganic Particles>

The dental resin composite material according to this embodiment contains inorganic particles. The blending of the inorganic particles is suitable from the viewpoints of: having an effect of making the dental resin composite material less liable to bend by enhancing its rigidity; improving abrasion resistance; having an effect of suppressing entanglement of the polyaryletherketone resin contained in the dental resin composite material to improve machinability in a step of processing a product, to thereby enhance processing efficiency; and the like. As the blending amount of the inorganic particles increases, the dental resin composite material has higher rigidity to become less liable to bend, but there is a tendency that brittle fracture is more liable to occur. As the blending amount of the inorganic particles increases, the abrasion resistance of the dental resin composite material improves, but there is a tendency that wear of a paired material is more liable to be caused. As the blending amount of the inorganic particles increases, shear heating during mixing of the inorganic particles and the raw material resin tends to increase, and hence it is considered that it becomes more difficult to obtain a dental resin composite material having a light and satisfactory color tone. In addition, as the blending amount of the inorganic particles increases, the effect of suppressing entanglement of the polyaryletherketone resin contained in the dental resin composite material increases, but there is a tendency that a machining tool wears earlier. The blending amount of the inorganic particles in the dental resin composite material according to this embodiment is from 10 parts by mass to 300 parts by mass, preferably from 42 parts by mass to 100 parts by mass with respect to 100 parts by mass of the polyaryletherketone resin.

As the inorganic particles, ones made of hitherto known various materials may be used. Specifically, there may be used, for example: glasses, such as silica glass, borosilicate glass, soda glass, aluminosilicate glass, and fluoroaluminosilicate glass; glass ceramics, such as crystallized glass obtained by depositing a crystal in any such glass, and crystallized glass obtained by depositing a crystal of diopside, leucite, or the like; composite inorganic oxides, such as silica-zirconia, silica-titania, and silica-alumina; oxides each obtained by adding a Group I metal oxide to any such composite oxide; and metal inorganic oxides, such as silica, alumina, titania, and zirconia. In particular, silica, silica-based particles each formed of a composite oxide of the silica and another metal oxide, titania, or titanium dioxide-based particles each formed of a composite oxide of the titania and another metal oxide are suitable because of having less harmfulness to a living body, and enabling production of a dental resin composite material having a light color tone and an excellent appearance.

In addition, an inorganic pigment is appropriately used as the inorganic particles in order to obtain a dental resin composite material having a desired color tone and appearance. The inorganic pigment is appropriately selected from inorganic particles of such various materials as listed above depending on the desired color tone and appearance. In addition, from the viewpoint of making the color tone of the dental resin composite material light, an inorganic pigment having a higher whiteness than the polyaryletherketone resin to be contained in the dental resin composite material may be used. Such inorganic pigment is appropriately selected on the basis of a relative relationship between the whiteness of the polyaryletherketone resin and the whiteness of the inorganic pigment, and may be generally exemplified by titanium dioxide-based particles, zinc oxide-based particles, barium sulfate-based particles, and the like. It is only required that at least part of the inorganic particles to be contained in the dental resin composite material have a function/role as an inorganic pigment for the purpose of obtaining the desired color tone and appearance, but the whole amount thereof may have a function/role as an inorganic pigment.

The shape of each of the inorganic particles is not particularly limited, and may be appropriately selected from a spherical shape, a substantially spherical shape, an amorphous shape, a needle shape, an aggregate shape, a cluster shape, and the like. It is generally preferred to use spherical or substantially spherical inorganic particles or powder obtained by aggregating the spherical or substantially spherical inorganic particles through heat treatment or the like. In addition, the average particle diameter of the inorganic particles is preferably from 0.01 µm to 10 µm, more preferably from 0.1 µm to 3 µm.

The surfaces of the inorganic particles are preferably hydrophobized for the purpose of improving their dispersibility in the polyaryletherketone resin. Such hydrophobizing surface treatment is not particularly limited, and a hitherto known method is adopted without any limitation.

A typical example of the surface treatment method is a method involving using a silane coupling agent or a titanate-based coupling agent as the hydrophobizing agent. With regard to the kind of such coupling agent, its use amount, and its treatment method, ones appropriately selected from hitherto known methods are adopted.

Other Blending Material

The dental resin composite material according to this embodiment may contain any other blending material as required as long as its color tone and appearance are not impaired. Examples of such material may include organic particles, organic-inorganic composite particles, glass fiber, an X-ray contrast medium, an antistatic, a UV absorber, a pigment, and a colorant.

Method of Producing Dental Resin Composite Material

The dental resin composite material according to this embodiment may be produced by utilizing a related-art production process for a dental resin composite material. For production of the dental resin composite material according to this embodiment, any known method including at least a step of mixing a polyaryletherketone resin and inorganic particles in a molten state (melt-mixing step) may be used. As an apparatus for the mixing, which may be of a batch type or a continuous type, a kneading machine, a kneader, an extrusion molding machine, or the like may be used. The polyaryletherketone resin and the inorganic particles may be mixed at the time of melting, or may be melted after being preliminarily mixed. The melt mixture in a high-temperature state obtained by the melt-mixing is first molded into a member for secondary processing having, for example, a pellet form, a powder form, or a block form, and then the member for secondary processing is molded into a target shape by, for example, extrusion molding, press molding, injection molding, laser forming, a layered manufacturing method, cutting processing, machining processing, or polishing processing, before use. In addition, the melt mixture in a high-temperature state may be directly molded into a target shape by extrusion molding, injection molding, or the like.

On the basis of such known production process as described above, a treatment method for adjusting the content of the impurity having an aromatic ring in the dental resin composite material to 90 ppm or less is further performed in a process starting with the production/procurement stage of the various raw materials to be used for producing the dental resin composite material according to this embodiment and ending with the completion of the dental resin composite material according to this embodiment.

Such treatment method is not particularly limited, and examples thereof include: (1) a method involving treating a resin composite material itself containing more than 90 ppm of the impurity having an aromatic ring produced by a hitherto known production method, to thereby obtain the dental resin composite material according to this embodiment; (2) a method involving performing heat treatment and deaeration of the impurity in the production steps of the dental resin composite material according to this embodiment; (3) a method involving suppressing the generation of the impurity having an aromatic ring in the production steps of the dental resin composite material according to this embodiment; (4) a method involving treating a raw material to be used for producing the dental resin composite material according to this embodiment; and (5) a method obtained by combining two or more methods out of the various methods exemplified in (1) to (4) and the like.

(1) Examples of the method involving treating the resin composite material itself include: a method involving repeatedly washing the resin composite material with an organic solvent, water, or the like; a method involving subjecting the resin composite material to heat treatment; and a method involving subjecting the resin composite material to heating treatment in pressurized water.

(2) In the method involving performing heat treatment and deaeration of the impurity in the production steps of the dental resin composite material according to this embodiment, when deaeration of the impurity having an aromatic ring generated by the heating of the dental resin composite material is performed, the dental resin composite material is heated to preferably a temperature equal to or higher than the glass transition temperature of the polyaryletherketone resin contained therein, more preferably a temperature equal to or higher than the melting point of the polyaryletherketone resin. With regard to the shape of the dental resin composite material at this time, a finely divided material cut/pulverized to have the form of films each having a thickness of 2 mm or less, fine particles, pellets, or blocks is preferably used because the effect of removing the impurity having an aromatic ring is increased by virtue of an increase in surface area. The finely divided material may be molded into a desired shape through a molding step.

Specific examples of the method involving performing heat treatment and deaeration in the production steps of the dental resin composite material according to this embodiment include: a method involving performing heating and deaeration at the time of mixing of raw material pellets or powder formed of the resin composite material; a method involving performing normal-pressure or reduced-pressure deaeration through a vent hole in the step of melt-mixing the polyaryletherketone resin and the inorganic particles; and a method involving using a vented injection molding machine in the step of molding the resin composite material. However, the effect of the heat treatment and deaeration in the production steps of the dental resin composite material according to this embodiment is limited because it is difficult to secure an area where deaeration can be performed for the material, and hence productivity is liable to reduce.

(3) Examples of the method involving suppressing the generation of the impurity having an aromatic ring in the production steps of the dental resin composite material according to this embodiment include: reduction of the amount of moisture adhering to any of the various raw materials or an intermediate by drying; prevention of overheating or overload in the melt-mixing step or the molding step; and introduction of an inert gas for preventing oxidation degradation over the entirety of the production steps.

(4) Examples of the method involving treating a raw material to be used for producing the dental resin composite material according to this embodiment include: a method involving repeatedly washing the polyaryletherketone resin or the inorganic particles to be used as a raw material with an organic solvent, water, or the like; a method involving performing heat treatment; and a method involving performing heating treatment in pressurized water. It is presumed that the impurity having an aromatic ring is mostly derived from the polyaryletherketone resin, and hence, in order to effectively reduce the concentration of the impurity having an aromatic ring, the polyaryletherketone resin to be used as a raw material is preferably subjected to heat treatment or heating treatment in pressurized water, particularly preferably heat treatment.

In this case, when the dental resin composite material according to this embodiment is produced through a heat treatment step of subjecting the polyaryletherketone resin to be used as a raw material to heat treatment, a main flow of a series of production steps is as described below. First, the polyaryletherketone resin (primary raw material resin) is prepared by synthesis or by the purchase of a commercially available product. Next, the primary raw material resin is subjected to heat treatment to reduce the concentration of the impurity having an aromatic ring in the primary raw material resin, to thereby obtain a secondary raw material resin. Then, with the use of the secondary raw material resin and the inorganic particles, at least the melt-mixing step is performed. Thus, the dental resin composite material according to this embodiment is obtained.

In the above-mentioned series of production processes, the content of the impurity having an aromatic ring in the secondary raw material resin is preferably 150 ppm or less, more preferably 100 ppm or less, still more preferably 30 ppm or less, particularly preferably 3 ppm or less, most preferably below the detection limit in measurement (0 ppm). However, in consideration of the fact that the content of the impurity having an aromatic ring is also reduced during melt-mixing using the secondary raw material resin and the inorganic particles, the content of the impurity having an aromatic ring in the secondary raw material resin may be more than 90 ppm and 150 ppm or less.

In addition, the content of the impurity having an aromatic ring in the primary raw material resin is generally more than 150 ppm. For example, the content of the impurity having an aromatic ring in a commercially available polyaryletherketone resin suitable for utilization as the primary raw material resin is generally more than 150 ppm and about 2,000 ppm or less. However, when the content of the impurity having an aromatic ring in the raw material resin procured by synthesis or by the purchase of a commercially available product is 150 ppm or less, it is preferred that the raw material resin be used as it is for the melt-mixing step.

In order to obtain the secondary raw material resin in which the content of the impurity having an aromatic ring is 150 ppm or less, it is preferred that the primary raw material resin be, for example, placed in a heat treatment apparatus set to a temperature in the range of from the glass transition temperature of the polyaryletherketone resin or more to less than the melting point of the polyaryletherketone resin, and heated for a certain period of time or longer. In this case, it is preferred that a volatile component containing the impurity having an aromatic ring generated from the primary raw material resin be effectively eliminated out of the system, or immobilized in the heat treatment apparatus, so as to prevent the volatile component containing the impurity having an aromatic ring from adhering again to the primary raw material resin. As a method of eliminating the volatile component, any method, such as replacement of an internal gas in the heat treatment apparatus (e.g., replacement of the internal gas by opening and shutting of a door or forced discharge of the internal gas with an air-blow device, such as an air-blow fan), an adsorbent capable of adsorbing the volatile component, arrangement of an adsorption filter, or heating on a hot plate in an open system, may be used.

The primary raw material resin to be subjected to the heat treatment preferably has the form of powder, and in this case, the average particle diameter of the powder is preferably 2,000 µm or less. As the average particle diameter of the powder decreases, the effect of removing the impurity having an aromatic ring by the heat treatment increases. As the average particle diameter of the powder increases, degradation by oxidation reduces. From the viewpoints of the effect of removing the impurity having an aromatic ring and the effect of suppressing degradation by oxidation, the average particle diameter of the powder is more preferably from 150 µm to 2,000 µm, still more preferably from 200 µm to 1,000 µm. As used herein, the term "average particle diameter" means a volume-average particle diameter measured by a laser diffraction/scattering method. The polyaryletherketone resin to be used as a raw material is available in various forms, such as powder, granules, pellets, rods, plates, and other molded articles. As the primary raw material resin to be subjected to the heat treatment, a powder grade may be used, a product obtained by further pulverizing and classifying the powder grade may be used, or a product prepared by pulverizing and classifying a resin having the form of, for example, granules, pellets, rods, plates, or any other molded article into a powder form may be used.

As the gas (internal gas) for filling the inside of the heat treatment apparatus, air may be used, or an inert gas may be used in order to prevent oxidation degradation. Specific examples of the inert gas include a carbon dioxide gas, a nitrogen gas, an argon gas, and a helium gas. In addition, as materials for the adsorbent and the adsorption filter, there are given, for example, activated carbon, a zeolite, activated alumina, silica gel, and ion exchange fiber. The adsorbent and the adsorption filter need to be replaced or regenerated after a certain period of time of use. When the adsorbent or the adsorption filter is used, it is preferred that the internal gas be efficiently brought into contact with the adsorbent or the adsorption filter by, for example, circulating the internal gas in the heat treatment apparatus.

A known apparatus may be used as the heat treatment apparatus to be used for the heat treatment. Specific examples thereof include: closed heat treatment apparatus, such as a box-type drying oven, a dry oven, a thermostatic chamber, a natural convection-type drying machine, a forced convection-type drying machine, an inert oven, and a conical dryer; and gas replacement-type heat treatment apparatus, such as an air-blow drying oven, a forced circulation-type heat aging tester, Geer's aging tester, a cell-shaped heat aging tester, and a natural ventilation-type heat aging tester. In addition, the heat treatment is preferably performed while the internal gas in the heat treatment apparatus is replaced continuously, intermittently, or appropriately. In this case, the replacement of the internal gas may be performed by manually opening and shutting a door of a closed heat treatment apparatus, but is more preferably performed using a gas replacement-type heat treatment apparatus, such as an air-blow drying machine having a forced ventilation mechanism based on a ventilation fan, or a heat aging tester, because the replacement of the internal gas can be efficiently performed. The number of times of replacement of the internal gas during the heat treatment step is preferably 1 or more from the viewpoint of the elimination efficiency of the volatile component, and is more preferably 2 or more, still more preferably from 10 to 60. Herein, the number of times refers to the number of times an equal volume of the gas to the internal volume of the heat treatment apparatus is replaced. When the air-blow drying oven is used, an air velocity is preferably from 1.5 m/s to 9.0 m/s. When the number of times of replacement of the internal gas is less than 1, the impurity-removing effect is low. This tendency becomes remarkable as the loading amount of the primary raw material resin powder increases with respect to the internal volume in the air-blow drying oven chamber. When the number of times of gas replacement is large, the primary raw material resin may undergo oxidation degradation, and besides, it is difficult to keep the temperature in the chamber at high temperature.

In addition, it is preferred from the viewpoint of promoting the diffusion of the volatile component that the primary raw material resin be stirred during the heat treatment step. The stirring of the primary raw material resin may be manually performed using a stirring rod or the like, or may use a mixer. Specific examples of an apparatus that may be utilized for such stirring include a V-type mixer, a W-type mixer, a fluidized bed drying machine, a rotary kiln, a rocking mixer, and a continuous airflow drying machine.

It is preferred that the heat treatment temperature in the case where the heat treatment is performed be appropriately selected within the temperature range from the glass transition temperature of the polyaryletherketone resin or more to less than the melting point of the polyaryletherketone resin. In this case, the lower limit value of the heat treatment temperature is more preferably a temperature of the glass transition temperature+80° C. or more, still more preferably a temperature of the glass transition temperature+90° C. or more.

In addition, the upper limit value of the heat treatment temperature is more preferably a temperature of the melting point−40° C. or less, still more preferably a temperature of the melting point−70° C. or less. When the heat treatment temperature is lower than the glass transition temperature, the effect of reducing the content of the impurity having an aromatic ring is hardly obtained. Meanwhile, when the heat treatment temperature is higher than the melting point, the following problems may occur: discoloration of the polyaryletherketone resin due to oxidation degradation, and changes in powder properties due to fusion/sticking of the polyaryletherketone resin powder. The glass transition temperature and melting point of the polyaryletherketone resin powder are determined by differential scanning calorimetry. As a measurement method, the measurement may be performed by a method in conformity with ASTM D3418-15. The period of time required for the heat treatment may be set to any period of time, but is preferably from 10 minutes to 24 hours, more preferably from 1 hour to 15 hours.

As described above, the dental resin composite material according to this embodiment may be produced by any of various production processes. Of those, the dental resin composite material according to this embodiment is particularly preferably produced by the following production process. That is, the dental resin composite material according to this embodiment is preferably produced by a production method including a step of mixing 100 parts by mass of a polyaryletherketone resin (A) containing 150 ppm or less of an impurity having an aromatic ring [raw material resin or secondary raw material resin] and 10 parts by mass to 300 parts by mass of inorganic particles in a molten state (melt-mixing step). In addition, in this case, the polyaryletherketone resin (A) containing 150 ppm or less of an impurity having an aromatic ring [secondary raw material resin] is preferably produced at least through a step of subjecting a polyaryletherketone resin powder (B) containing the impurity having an aromatic ring [powder of primary raw material resin] to heating treatment in the temperature range of from the glass transition temperature of the polyaryletherketone resin powder (B) [powder of the primary raw material resin] or more to less than the melting point of the polyaryletherketone resin powder (B) [powder of the primary raw material resin] in a heat treatment apparatus while replacing a gas in the heat treatment apparatus (internal gas) (heat treatment step).

Applications

The dental resin composite material according to this embodiment is suitable as, for example, an artificial tooth, a dental crown restoration material, a dental plate material, an orthodontic wire, a bracket, or an artificial abutment. In addition, with regard to a preferred color tone of a dental material obtained by molding/processing the dental resin composite material according to this embodiment into a desired shape, the lightness L* value of a molded body of the dental resin composite material having a thickness of 1 mm in a CIELab color system is preferably 82.5 or more, more preferably 84.5 or more, most preferably 86.0 or more against a black background because a light and natural appearance is exhibited in an oral cavity.

EXAMPLES

The present invention is hereinafter described in more detail by way of Examples. However, the present invention is not limited to these Examples.

Materials, test methods, and the like to be used in Examples and Comparative Examples are described below.

Measurement Method for Glass Transition Temperature and Melting Point

The glass transition temperature and melting point of a polyaryletherketone resin were measured in conformity with a method described in ASTM D3418-15 using a differential scanning calorimeter under the conditions of an initial temperature of 40° C., a temperature increase rate of 20° C./min, a reaching temperature of 350° C., a holding time of 5 minutes, and a temperature decrease rate of 20° C./min.

Measurement Method for Volume-Average Particle Diameter

For a polyaryletherketone resin of a powder form, its volume-average particle diameter was determined using a laser diffraction/scattering particle size analyzer.

Measurement Method for Content of Impurity Having Aromatic Ring in Polyaryletherketone Resin (Raw Material Resin) Powder Analysis of an impurity having an aromatic ring was performed using a GC/MS (Gas Chromatograph/Mass Spectrometer) with a thermal desorption apparatus. Multi-shot Pyrolyzer EGA/PY-3030D manufactured by Frontier Lab was used as the thermal desorption apparatus. A disposable eco cup PY1-EC80F was used as a sample container, and 7890B GC system manufactured by Agilent Technologies was used as the gas chromatograph. DB1-MS manufactured by Agilent Technologies (L: 30 m, D: 0.25 mm, Film: 0.25 µm) was used as a column. JMS-Q1500GC manufactured by JEOL Ltd. was used as the mass spectrometer. In the thermal desorption apparatus, temperature increase conditions were set as follows: initial temperature: 50° C., temperature increase rate: 600° C./min, reaching temperature: a temperature higher than the melting point of polyaryletherketone resin powder subjected to the measurement by 60° C. (±5° C.), and holding time: 10 minutes. In addition, a temperature at an interface between the thermal desorption apparatus and the gas chromatograph was set to from 280° C. to 300° C.

The temperature increase conditions of the gas chromatograph were set to an initial temperature of 40° C., a temperature increase rate of 20° C./min, and a reaching temperature of 350° C., and its inlet temperature was set to 280° C. A helium gas was used as a carrier gas, and a gas flow rate was set to 1.0 mL/min. The mass spectrometer employed an EI method as an ionization method, and was set to an ionizing current value of 50 µA, an ionization energy of 70 eV, an ion source temperature of 250° C., and a GC-IF temperature of 250° C. Quantification and identification were performed for peaks during a period in which the temperature was increased from 40° C. to 350° C. The sample holder having placed therein 0.0020 g to 0.0030 g of the polyaryletherketone resin powder was placed in the thermal desorption apparatus. Next, measurement was initiated, and the resultant chromatogram and mass spectrum were used to perform analysis. For the quantification, a calibration curve was prepared using diphenyl sulfone as a standard substance with the gas chromatograph, and the concentration of each impurity containing an aromatic ring was determined from its respective peak area by an external standard method. Measurement was repeated until the measured value of an (n+1)-th measurement became less than 5% of an n-th measured value. In addition, each measurement was performed under exactly the same conditions. Then, a value obtained by summing up the first measured value to the (n+1)-th measured value was determined as the "content of the impurity having an aromatic ring." Of the measured compounds each having an aromatic ring, each kind of compound had a molecular weight of less than 1,000.

Measurement Method for Content of Impurity having Aromatic Ring in Dental Resin Composite Material 0.01 g to 0.03 g of a cut material obtained by cutting a molded body of a dental resin composite material into a small piece measuring about 2 mm or less on each side was weighed and placed in a sample holder, and then the sample holder was placed in a thermal desorption apparatus. Next, analysis of an impurity having an aromatic ring was performed using a GC/MS. 7890B GC system manufactured by Agilent Technologies was used as the gas chromatograph. DB1-MS manufactured by Agilent Technologies (L: 30 m, D: 0.25 mm, Film: 0.25 µm) was used as a column. JMS-Q1500GC manufactured by JEOL Ltd. was used as the mass spectrometer. The temperature increase conditions of the gas chromatograph were set to an initial temperature of 40° C., a temperature increase rate of 20° C./min, and a reaching temperature of 350° C., and its inlet temperature was set to 280° C. A helium gas was used as a carrier gas, and a gas flow rate was set to 1.0 mL/min. The mass spectrometer employed an EI method as an ionization method, and was set to an ionizing current value of 50 µA, an ionization energy of 70 eV, an ion source temperature of 250° C., and a GC-IF temperature of 250° C. Quantification and identification were performed for peaks during a period in which the temperature was increased from 40° C. to 350° C. Measurement was initiated, and the resultant chromatogram and mass spectrum were used to perform analysis. For the quantification, a calibration curve was prepared using diphenyl sulfone as a standard substance with the gas chromatograph, and the concentration of each impurity containing an aromatic ring in the dental resin composite material was determined from its respective peak area by an external standard method.

The content of the impurity having an aromatic ring in the dental resin composite material was measured using the GC/MS with the thermal desorption apparatus in the same manner as in the measurement method described in the <Measurement Method for Content of Impurity having Aromatic Ring in Polyaryletherketone Resin (Raw Material Resin) Powder> section except for the matters described above. Of the measured compounds each having an aromatic ring, each kind of compound had a molecular weight of less than 1,000.

Measurement Method for Content of Acetone-Soluble Component in Acetone Extract Solution of Dental Resin Composite Material For reference, the content of an acetone-soluble component in an acetone extract solution obtained by immersing a dental resin composite material in acetone was also measured. First, 1.0 g of a cut material obtained by cutting a molded body of the dental resin composite material into a small piece measuring about 2 mm or less on each side was put into a test tube, and then 10 ml of acetone was further added. The test tube was stirred under room temperature for 24 hours to dissolve the acetone-soluble component contained in the cut material (dental resin composite material) into an acetone solution. The contents in the test tube were filtered through a membrane filter to be separated into a residue (cut material after acetone immersion) and a filtrate (acetone extract solution). Next, the acetone extract solution was introduced into a gas chromatograph through the use of a syringe, and the content of the acetone-soluble component in the acetone extract solution was measured. In this case, the measurement was performed in the same manner as in the measurement method described in the <Measurement Method for Content of Impurity having Aromatic Ring in Dental Resin Composite Material> section except for the matters described above. Of the measured compounds each having an aromatic ring, each kind of compound had a molecular weight of less than 1,000.

Measurement Method for Lightness L* of Polyaryletherketone Resin (Raw Material Resin) Powder Polyetheretherketone resin powder was loaded in a half amount into a 20 cc screw-capped vial, followed by capping, and a color tone was measured against a black background using a colorimeter (TC-1500MK-II, manufactured by Tokyo Denshoku Co., Ltd.) to determine a lightness L* value in a CIELab color system.

Measurement Method for Lightness L* of Dental Resin Composite Material

A molded body of a dental resin composite material measuring 12 mm long×14 mm wide×1 mm thick was produced, and then the surface of the molded body was buffed into a glossy surface using alumina as an abrasive. Next, the glossy surface of the molded body after the buffing was measured for a color tone against a black background using a colorimeter (TC-1500MK-II, manufactured by Tokyo Denshoku Co., Ltd.) to determine a lightness L* value in a CIELab color system.

Evaluation Method for Appearance of Dental Resin Composite Material

A molded body of a dental resin composite material measuring 12 mm long×14 mm wide×1 mm thick was produced, and then the surface of the molded body was buffed into a glossy surface using alumina as an abrasive. Next, the glossy surface of the molded body after the buffing was visually evaluated by the following evaluation criteria.
A: The color tone of the dental resin composite material is light and corresponds to B1 using the VITA classical shade guide as a color sample, and the dental resin composite material has no burning and no color unevenness.
B: The color tone of the dental resin composite material is slightly light and corresponds to A1 using the VITA classical shade guide as a color sample, and the dental resin composite material has little burning and little color unevenness.
C: The color tone of the dental resin composite material is dark and corresponds to C1 using the VITA classical shade guide as a color sample, and the dental resin composite material has no burning and no color unevenness.
D: The color tone of the dental resin composite material is dark and corresponds to C1 using the VITA classical shade guide as a color sample, and the dental resin composite material has burning and color unevenness.

Example 1

1 kg of polyetheretherketone resin powder (VESTAKEEP 2000P, Evonik, average particle diameter: 500 μm, melting point: 343° C., glass transition temperature: 150° C., initial content of impurity having aromatic ring: 234 ppm) was loaded into an aluminum vat (280 mm×210 mm×35 mm) so as to have a powder thickness of 25 mm, and was subjected to heat treatment with an air-blow drying oven Fine Oven DF412 manufactured by Yamato Scientific Co., Ltd. (gas replacement-type heat treatment apparatus). A temperature was set to 250° C., a heating time was set to 5 hours, and air replacement was set to be automatically performed 50 times per hour in a continuous manner.

The results of the various measurements and evaluation of the polyetheretherketone resin powder after heat treatment used for producing a dental resin composite material are as shown below.

Content of impurity having aromatic ring: 0 ppm

Visual evaluation of appearance and color tone: Coloration and color unevenness were not observed (comparable to the polyetheretherketone resin powder before heat treatment)

Lightness: $L^*=78.5$

60 Parts by mass of the polyetheretherketone resin powder after heat treatment, 30 parts by mass of amorphous silica having an average particle diameter of 2.0 μm (manufactured by Tokuyama Corporation), and 10 parts by mass of rutile titanium dioxide powder having an average particle diameter of 0.25 μm (Ishihara Sangyo Kaisha, Ltd., CR50) were mixed to uniformity. The resultant mixture was melt-kneaded with a twin-screw extrusion molding machine, and then pelletized with a pelletizer at φ2 mm and an interval of 3 mm to provide a dental resin composite material. A molded body of the dental resin composite material was obtained from the pellets by injection molding into a block shape measuring 12 mm×14 mm×18 mm using an injection molding machine. The results of the various measurements and evaluation are shown below.

(1) Content of acetone-soluble component in acetone extract solution of molded body: 0 ppm (2) Content of impurity having aromatic ring in molded body: 0 ppm (3) Lightness of molded body: $L^*=87.9$ (4) Result of appearance evaluation of molded body: A Example 2

Polyetheretherketone resin powder was subjected to heat treatment in the same manner as in Example 1 except that Geer's heat aging tester STD45 manufactured by Toyo Seiki Seisaku-sho, Ltd. (gas replacement-type heat treatment apparatus) was used as a heat treatment apparatus, and was set to a temperature of 250° C. and a heating time of 5 hours and set to automatically perform air replacement 10 times per hour in a continuous manner.

The results of the various measurements and evaluation of the polyetheretherketone resin powder after heat treatment used for producing a dental resin composite material are as shown below.

Content of impurity having aromatic ring: 10 ppm
Detected main impurity having aromatic ring: diphenyl sulfone
Visual evaluation of appearance and color tone: Coloration and color unevenness were not observed (comparable to the polyetheretherketone resin powder before heat treatment)
Lightness: $L^*=78.5$ With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 0 ppm
(2) Content of impurity having aromatic ring in molded body: 6 ppm
Detected main impurity having aromatic ring: diphenyl sulfone
(3) Lightness of molded body: $L^*=86.1$
(4) Result of appearance evaluation of molded body: A Example 3

Polyetheretherketone resin powder was loaded into an aluminum vat (280 mm×210 mm×35 mm) so as to have a powder thickness of 45 mm, and was subjected to heat treatment in the same manner as in Example 1 except that Geer's heat aging tester STD45 manufactured by Toyo Seiki Seisaku-sho, Ltd. (gas replacement-type heat treatment apparatus) was used as a heat treatment apparatus, and was set to a temperature of 250° C. and a heating time of 5 hours and set to automatically perform air replacement 10 times per hour in a continuous manner.

The results of the various measurements and evaluation of the polyetheretherketone resin powder after heat treatment used for producing a dental resin composite material are as shown below.

Content of impurity having aromatic ring: 122 ppm
Detected main impurities each having aromatic ring: diphenyl sulfone, 4,4'-difluorobenzophenone, and trans-4,4'-difluorochalcone
Visual evaluation of appearance and color tone: Coloration and color unevenness were not observed (comparable to the polyetheretherketone resin powder before heat treatment)
Lightness: $L^*=78.5$ With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 2 ppm
(2) Content of impurity having aromatic ring in molded body: 73 ppm
Detected main impurities each having aromatic ring: diphenyl sulfone and trans-4,4'-difluorochalcone
(3) Lightness of molded body: $L^*=84.0$
(4) Result of appearance evaluation of molded body: C Example 4

Polyetheretherketone resin powder was subjected to heat treatment in the same manner as in Example 1 except that Geer's heat aging tester STD45 manufactured by Toyo Seiki Seisaku-sho, Ltd. (gas replacement-type heat treatment apparatus) was used as a heat treatment apparatus, and was set to a temperature of 300° C. and a heating time of 5 hours and set to automatically perform air replacement 10 times per hour in a continuous manner.

The results of the various measurements and evaluation of the polyetheretherketone resin powder after heat treatment used for producing a dental resin composite material are as shown below.

Content of impurity having aromatic ring: 0 ppm
Visual evaluation of appearance and color tone: Coloration and color unevenness were not observed (comparable to the polyetheretherketone resin powder before heat treatment)
Lightness: $L^*=78.3$ With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 0 ppm
(2) Content of impurity having aromatic ring in molded body: 0 ppm
(3) Lightness of molded body: $L^*=87.6$
(4) Result of appearance evaluation of molded body: A Example 5

A molded body of a dental resin composite material was obtained by the method described in Example 1 except that 80 parts by mass of polyetheretherketone resin powder subjected to heat treatment by the same method as that of Example 1, 15 parts by mass of amorphous silica having an average particle diameter of 2.0 μm (manufactured by Tokuyama Corporation), and 5 parts by mass of rutile titanium dioxide powder having an average particle diameter of 0.25 μm (Ishihara Sangyo Kaisha, Ltd., CR50) were mixed to uniformity. The results of the various measurements and evaluation are shown below.
(1) Content of acetone-soluble component in acetone extract solution of molded body: 0 ppm
(2) Content of impurity having aromatic ring in molded body: 0 ppm
(3) Lightness of molded body: $L^*=85.2$
(4) Result of appearance evaluation of molded body: B Example 6

A molded body of a dental resin composite material was obtained by the method described in Example 1 except that 40 parts by mass of polyetheretherketone resin powder subjected to heat treatment by the same method as that of Example 1, 50 parts by mass of amorphous silica having an average particle diameter of 2.0 μm (manufactured by Tokuyama Corporation), and 10 parts by mass of rutile titanium dioxide powder having an average particle diameter of 0.25 μm (Ishihara Sangyo Kaisha, Ltd., CR50) were mixed to uniformity. The results of the various measurements and evaluation are shown below.
(1) Content of acetone-soluble component in acetone extract solution of molded body: 0 ppm
(2) Content of impurity having aromatic ring in molded body: 0 ppm
(3) Lightness of molded body: $L^*=86.8$
(4) Result of appearance evaluation of molded body: A Example 7

Heat treatment was performed by the same method as that of Example 1 except that polyetheretherketone resin powder (VESTAKEEP 4000P, Evonik, average particle diameter: 500 μm, melting point: 343° C., glass transition temperature: 152° C., initial content of impurity having aromatic ring: 550 ppm) was used.

The results of the various measurements and evaluation of the polyetheretherketone resin powder after heat treatment used for producing a dental resin composite material are as shown below.

Content of impurity having aromatic ring: 22 ppm
Detected main impurity having aromatic ring: diphenyl sulfone
Visual evaluation of appearance and color tone: Coloration and color unevenness were not observed (comparable to the polyetheretherketone resin powder before heat treatment)
Lightness: $L^*=77.6$ With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 0 ppm
(2) Content of impurity having aromatic ring in molded body: 13 ppm
Detected main impurity having aromatic ring: diphenyl sulfone
(3) Lightness of molded body: $L^*=86.2$
(4) Result of appearance evaluation of molded body: A Example 8

Heat treatment was performed by the same method as that of Example 1 except that: polyetheretherketone resin powder (VESTAKEEP 4000P, Evonik, average particle diameter: 500 μm, melting point: 343° C., glass transition temperature: 152° C., initial content of impurity having aromatic ring: 550 ppm) was used; and Geer's heat aging tester STD45 manufactured by Toyo Seiki Seisaku-sho, Ltd. (gas replacement-type heat treatment apparatus) was used as a heat treatment apparatus, and was set to a temperature of 250° C. and a heating time of 5 hours and set to automatically perform air replacement 10 times per hour in a continuous manner.

The results of the various measurements and evaluation of the polyetheretherketone resin powder after heat treatment used for producing a dental resin composite material are as shown below.

Content of impurity having aromatic ring: 33 ppm
Detected main impurities each having aromatic ring: diphenyl sulfone and trans-4,4'-difluorochalcone
Visual evaluation of appearance and color tone: Coloration and color unevenness were not observed (comparable to the polyetheretherketone resin powder before heat treatment)
Lightness: $L^*=77.6$ With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 1 ppm
(2) Content of impurity having aromatic ring in molded body: 20 ppm
Detected main impurities each having aromatic ring: diphenyl sulfone and trans-4,4'-difluorochalcone
(3) Lightness of molded body: $L^*=85.9$
(4) Result of appearance evaluation of molded body: B Example 9

Heat treatment was performed by the same method as that of Example 1 except that: polyetheretherketone resin powder (VESTAKEEP 4000P, Evonik, average particle diameter: 500 μm, melting point: 343° C., glass transition temperature: 152° C., initial content of impurity having aromatic ring: 550 ppm) was used; and Geer's heat aging tester STD45 manufactured by Toyo Seiki Seisaku-sho, Ltd. (gas replacement-type heat treatment apparatus) was used as a heat treatment apparatus, and was set to a temperature of 300° C. and a heating time of 5 hours and set to automatically perform air replacement 10 times per hour in a continuous manner.

The results of the various measurements and evaluation of the polyetheretherketone resin powder after heat treatment used for producing a dental resin composite material are as shown below.

Content of impurity having aromatic ring: 11 ppm
Detected main impurity having aromatic ring: diphenyl sulfone
Visual evaluation of appearance and color tone: Coloration and color unevenness were not observed (comparable to the polyetheretherketone resin powder before heat treatment)
Lightness: $L^*=77.4$ With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 0 ppm
(2) Content of impurity having aromatic ring in molded body: 7 ppm Detected main impurity having aromatic ring: diphenyl sulfone
(3) Lightness of molded body: L*=86.6
(4) Result of appearance evaluation of molded body: A Example 10

Heat treatment was performed by the same method as that of Example 1 except that: polyetheretherketone resin powder (VESTAKEEP 4000P, Evonik, average particle diameter: 500 μm, melting point: 343° C., glass transition temperature: 152° C., initial content of impurity having aromatic ring: 550 ppm) was used; and an air-blow drying oven Fine Oven DF412 manufactured by Yamato Scientific Co., Ltd. (gas replacement-type heat treatment apparatus) was used as a heat treatment apparatus, and was set to a temperature of 250° C. and a heating time of 5 hours and set to automatically perform air replacement 2 times per hour in a continuous manner.

The results of the various measurements and evaluation of the polyetheretherketone resin powder after heat treatment used for producing a dental resin composite material are as shown below.

Content of impurity having aromatic ring: 118 ppm
Detected main impurities each having aromatic ring: diphenyl sulfone, 4,4'-difluorobenzophenone, and trans-4,4'-difluorochalcone
Visual evaluation of appearance and color tone: Coloration and color unevenness were not observed (comparable to the polyetheretherketone resin powder before heat treatment)
Lightness: L*=77.6
Pellets of a dental resin composite material were obtained by the method described in Example 1 except that 80 parts by mass of the polyetheretherketone resin powder after heat treatment, 15 parts by mass of amorphous silica having an average particle diameter of 2.0 μm (manufactured by Tokuyama Corporation), and 5 parts by mass of rutile titanium dioxide powder having an average particle diameter of 0.25 μm (Ishihara Sangyo Kaisha, Ltd., CR50) were mixed to uniformity. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 2 ppm
(2) Content of impurity having aromatic ring in molded body: 89 ppm
Detected main impurities each having aromatic ring: diphenyl sulfone, 4,4'-difluorobenzophenone, and trans-4,4'-difluorochalcone
(3) Lightness of molded body: L*=83.6
(4) Result of appearance evaluation of molded body: C Example 11

A molded body of a dental resin composite material was obtained by the method described in Example 1 except that 40 parts by mass of the polyetheretherketone resin powder after heat treatment of Example 7, 50 parts by mass of amorphous silica having an average particle diameter of 2.0 μm (manufactured by Tokuyama Corporation), and 10 parts by mass of rutile titanium dioxide powder having an average particle diameter of 0.25 μm (Ishihara Sangyo Kaisha, Ltd., CR50) were mixed to uniformity. The results of the various measurements and evaluation are shown below.
(1) Content of acetone-soluble component in acetone extract solution of molded body: 0 ppm
(2) Content of impurity having aromatic ring in molded body: 9 ppm
Detected main impurity having aromatic ring: diphenyl sulfone
(3) Lightness of molded body: L*=86.5
(4) Result of appearance evaluation of molded body: A Example 12

Heat treatment was performed by the same method as that of Example 1 except that polyetheretherketone resin powder (380P, Victrex plc, average particle diameter: 1,500 μm, melting point: 343° C., glass transition temperature: 143° C., initial content of impurity having aromatic ring: 248 ppm) was used.

The results of the various measurements and evaluation of the polyetheretherketone resin powder after heat treatment used for producing a dental resin composite material are as shown below.

Content of impurity having aromatic ring: 69 ppm
Detected main impurity having aromatic ring: diphenyl sulfone
Visual evaluation of appearance and color tone: Coloration and color unevenness were not observed (comparable to the polyetheretherketone resin powder before heat treatment)
Lightness: L*=76.1
With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 1 ppm
(2) Content of impurity having aromatic ring in molded body: 38 ppm
Detected main impurity having aromatic ring: diphenyl sulfone
(3) Lightness of molded body: L*=85.3
(4) Result of appearance evaluation of molded body: B Example 13

Heat treatment was performed by the same method as that of Example 1 except that: polyetheretherketone resin powder (380P, Victrex plc, average particle diameter: 1,500 μm, melting point: 343° C., glass transition temperature: 143° C., initial content of impurity having aromatic ring: 248 ppm) was used; and Geer's heat aging tester STD45 manufactured by Toyo Seiki Seisaku-sho, Ltd. (gas replacement-type heat treatment apparatus) was used as a heat treatment apparatus, and was set to a temperature of 250° C. and a heating time of 5 hours and set to automatically perform air replacement 10 times per hour in a continuous manner.

The results of the various measurements and evaluation of the polyetheretherketone resin powder after heat treatment used for producing a dental resin composite material are as shown below.

Content of impurity having aromatic ring: 74 ppm

Detected main impurity having aromatic ring: diphenyl sulfone

Visual evaluation of appearance and color tone: Coloration and color unevenness were not observed (comparable to the polyetheretherketone resin powder before heat treatment)

Lightness: $L^*$=76.1

With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.

(1) Content of acetone-soluble component in acetone extract solution of molded body: 1 ppm (2) Content of impurity having aromatic ring in molded body: 45 ppm Detected main impurity having aromatic ring: diphenyl sulfone (3) Lightness of molded body: $L^*$=84.5

(4) Result of appearance evaluation of molded body: B

Example 14

Heat treatment was performed by the same method as that of Example 1 except that: polyetheretherketone resin powder (380P, Victrex plc, average particle diameter: 1,500 μm, melting point: 343° C., glass transition temperature: 143° C., initial content of impurity having aromatic ring: 248 ppm) was used; and Geer's heat aging tester STD45 manufactured by Toyo Seiki Seisaku-sho, Ltd. (gas replacement-type heat treatment apparatus) was used as a heat treatment apparatus, and was set to a temperature of 300° C. and a heating time of 5 hours and set to automatically perform air replacement 10 times per hour in a continuous manner.

The results of the various measurements and evaluation of the polyetheretherketone resin powder after heat treatment used for producing a dental resin composite material are as shown below.

Content of impurity having aromatic ring: 35 ppm

Detected main impurity having aromatic ring: diphenyl sulfone

Visual evaluation of appearance and color tone: Coloration and color unevenness were not observed (comparable to the polyetheretherketone resin powder before heat treatment)

Lightness: $L^*$=75.9

With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.

(1) Content of acetone-soluble component in acetone extract solution of molded body: 1 ppm (2) Content of impurity having aromatic ring in molded body: 21 ppm Detected main impurity having aromatic ring: diphenyl sulfone (3) Lightness of molded body: $L^*$=85.8

(4) Result of appearance evaluation of molded body: B

Example 15

A molded body of a dental resin composite material was obtained by the method described in Example 1 except that 80 parts by mass of the resin powder after heat treatment of Example 12, 10 parts by mass of amorphous silica having an average particle diameter of 2.0 μm (manufactured by Tokuyama Corporation), and 5 parts by mass of rutile titanium dioxide powder having an average particle diameter of 0.25 μm (Ishihara Sangyo Kaisha, Ltd., CR50) were mixed to uniformity. The results of the various measurements and evaluation are shown below.

(1) Content of acetone-soluble component in acetone extract solution of molded body: 1 ppm (2) Content of impurity having aromatic ring in molded body: 56 ppm Detected main impurity having aromatic ring: diphenyl sulfone (3) Lightness of molded body: $L^*$=83.9

(4) Result of appearance evaluation of molded body: C

Example 16

A molded body of a dental resin composite material was obtained by the method described in Example 1 except that 40 parts by mass of the resin powder after heat treatment of Example 12, 50 parts by mass of amorphous silica having an average particle diameter of 2.0 μm (manufactured by Tokuyama Corporation), and 10 parts by mass of rutile titanium dioxide powder having an average particle diameter of 0.25 μm (Ishihara Sangyo Kaisha, Ltd., CR50) were mixed to uniformity. The results of the various measurements and evaluation are shown below.

(1) Content of acetone-soluble component in acetone extract solution of molded body: 1 ppm (2) Content of impurity having aromatic ring in molded body: 28 ppm Detected main impurity having aromatic ring: diphenyl sulfone (3) Lightness of molded body: $L^*$=85.4

(4) Result of appearance evaluation of molded body: B

Example 17

Heat treatment was performed by the same method as that of Example 1 except that polyetheretherketone resin powder (150P, Victrex plc, average particle diameter: 1,500 μm, melting point: 343° C., glass transition temperature: 143° C., initial content of impurity having aromatic ring: 544 ppm) was used.

The results of the various measurements and evaluation of the polyetheretherketone resin powder after heat treatment used for producing a dental resin composite material are as shown below.

Content of impurity having aromatic ring: 141 ppm

Detected main impurities each having aromatic ring: diphenyl sulfone, 4-phenoxybenzaldehyde, and bis(4-phenoxyphenyl)methanone Visual evaluation of appearance and color tone: Coloration and color unevenness were not observed (comparable to the polyetheretherketone resin powder before heat treatment)
Lightness: L*=76.3

With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 2 ppm
(2) Content of impurity having aromatic ring in molded body: 85 ppm
Detected main impurities each having aromatic ring: diphenyl sulfone, 4-phenoxybenzaldehyde, and bis(4-phenoxyphenyl)methanone
(3) Lightness of molded body: L*=83.0
(4) Result of appearance evaluation of molded body: C Example 18

Heat treatment was performed by the same method as that of Example 1 except that: polyetheretherketone resin powder (150P, Victrex plc, average particle diameter: 1,500 µm, melting point: 343° C., glass transition temperature: 143° C., initial content of impurity having aromatic ring: 544 ppm) was used; and Geer's heat aging tester STD45 manufactured by Toyo Seiki Seisaku-sho, Ltd. (gas replacement-type heat treatment apparatus) was used as a heat treatment apparatus, and was set to a temperature of 300° C. and a heating time of 5 hours and set to automatically perform air replacement 10 times per hour in a continuous manner.

The results of the various measurements and evaluation of the polyetheretherketone resin powder after heat treatment used for producing a dental resin composite material are as shown below.
Content of impurity having aromatic ring: 71 ppm
Detected main impurity having aromatic ring: diphenyl sulfone
Visual evaluation of appearance and color tone: Coloration and color unevenness were not observed (comparable to the polyetheretherketone resin powder before heat treatment)
Lightness: L*=76.1

With the use of the polyetheretherketone resin powder after heat treatment, pellets of a dental resin composite material were obtained by the same method as that of Example 1. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 1 ppm
(2) Content of impurity having aromatic ring in molded body: 42 ppm
Detected main impurity having aromatic ring: diphenyl sulfone
(3) Lightness of molded body: L*=84.6
(4) Result of appearance evaluation of molded body: B Example 19

A molded body of a dental resin composite material was obtained by the method described in Example 1 except that 40 parts by mass of the resin powder after heat treatment of Example 17, 50 parts by mass of amorphous silica having an average particle diameter of 2.0 µm (manufactured by Tokuyama Corporation), and 10 parts by mass of rutile titanium dioxide powder having an average particle diameter of 0.25 µm (Ishihara Sangyo Kaisha, Ltd., CR50) were mixed to uniformity. The results of the various measurements and evaluation are shown below.
(1) Content of acetone-soluble component in acetone extract solution of molded body: 2 ppm
(2) Content of impurity having aromatic ring in molded body: 57 ppm
Detected main impurity having aromatic ring: diphenyl sulfone
(3) Lightness of molded body: L*=83.9
(4) Result of appearance evaluation of molded body: C Comparative Example 1

As a raw material for a dental resin composite material, commercially available polyetheretherketone resin powder (VESTAKEEP 2000P, Evonik, average particle diameter: 500 µm, melting point: 343° C., glass transition temperature: 150° C., initial content of impurity: 234 ppm) was used as it was without heat treatment. The L* value of the polyetheretherketone resin powder (without heat treatment) serving as an indicator of lightness was L*=78.7.

60 Parts by mass of the polyetheretherketone resin powder (without heat treatment), 30 parts by mass of amorphous silica having an average particle diameter of 2.0 µm (manufactured by Tokuyama Corporation), and 10 parts by mass of rutile titanium dioxide powder having an average particle diameter of 0.25 µm (Ishihara Sangyo Kaisha, Ltd., CR50) were mixed to uniformity. The resultant mixture was melt-kneaded with a twin-screw extrusion molding machine, and then pelletized with a pelletizer at φ2 mm and an interval of 3 mm to provide a dental resin composite material. A molded body of the dental resin composite material was obtained from the pellets by injection molding into a block shape measuring 12 mm×14 mm×18 mm using an injection molding machine. The results of the various measurements and evaluation are shown below.
(1) Content of acetone-soluble component in acetone extract solution of molded body: 6 ppm
(2) Content of impurity having aromatic ring in molded body: 137 ppm
Detected main impurities each having aromatic ring: diphenyl sulfone, 4,4'-difluorobenzophenone, trans-4,4'-difluorochalcone, and biphenyl
(3) Lightness of molded body: L*=79.0
(4) Result of appearance evaluation of molded body: D Comparative Example 2

1 kg of polyetheretherketone resin powder (VESTAKEEP 2000P, Evonik, average particle diameter: 500 µm, melting point: 343° C., glass transition temperature: 150° C., initial content of impurity: 234 ppm) was loaded into an aluminum vat (280 mm×210 mm×35 mm) so as to have a powder thickness of 25 mm, and was subjected to heat treatment with an air-blow drying oven Fine Oven DF412 manufactured by Yamato Scientific Co., Ltd. (gas replacement-type heat treatment apparatus). A temperature was set to 250° C., a heating time was set to 5 hours, and air in the air-blow drying oven was internally circulated constantly.

The results of the various measurements and evaluation of the polyetheretherketone resin powder after heat treatment used for producing a dental resin composite material are as shown below.

Content of impurity having aromatic ring: 154 ppm

Detected main impurities each having aromatic ring: diphenyl sulfone, 4,4'-difluorobenzophenone, trans-4,4'-difluorochalcone, and biphenyl Visual evaluation of appearance and color tone: Coloration and color unevenness were not observed (comparable to the polyetheretherketone resin powder before heat treatment)

Lightness: L*=78.6

A molded body of a dental resin composite material was obtained by the same method as that of Comparative Example 1 except that 60 parts by mass of the polyetheretherketone resin powder after heat treatment was used. The results of the various measurements and evaluation are shown below.
(1) Content of acetone-soluble component in acetone extract solution of molded body: 3 ppm
(2) Content of impurity having aromatic ring in molded body: 92 ppm Detected main impurities each having aromatic ring: diphenyl sulfone, 4,4'-difluorobenzophenone, trans-4,4'-difluorochalcone, and biphenyl
(3) Lightness of molded body: L*=82.1
(4) Result of appearance evaluation of molded body: D Comparative Example 3

As a raw material for a dental resin composite material, commercially available polyetheretherketone resin powder (VESTAKEEP 4000P, Evonik, average particle diameter: 500 μm, melting point: 343° C., glass transition temperature: 152° C., initial content of impurity having aromatic ring: 550 ppm) was used as it was without heat treatment. The L* value of the polyetheretherketone resin powder (without heat treatment) serving as an indicator of lightness was L*=77.6.

A molded body of a dental resin composite material was obtained by the same method as that of Comparative Example 1 except that 60 parts by mass of the polyetheretherketone resin powder (without heat treatment) was used. The results of the various measurements and evaluation are shown below.
(1) Content of acetone-soluble component in acetone extract solution of molded body: 10 ppm
(2) Content of impurity having aromatic ring in molded body: 330 ppm Detected main impurities each having aromatic ring: diphenyl sulfone, 4,4'-difluorobenzophenone, trans-4,4'-difluorochalcone, and biphenyl
(3) Lightness of molded body: L*=77.3
(4) Result of appearance evaluation of molded body: D Comparative Example 4

As a raw material for a dental resin composite material, commercially available polyetheretherketone resin powder (380P, Victrex plc, average particle diameter: 1,500 μm, melting point: 343° C., glass transition temperature: 143° C., initial content of impurity having aromatic ring: 248 ppm) was used as it was without heat treatment. The L* value of the polyetheretherketone resin powder (without heat treatment) serving as an indicator of lightness was L*=76.1.

A molded body of a dental resin composite material was obtained by the same method as that of Comparative Example 1 except that 60 parts by mass of the polyetheretherketone resin powder (without heat treatment) was used. The results of the various measurements and evaluation are shown below.
(1) Content of acetone-soluble component in acetone extract solution of molded body: 4 ppm
(2) Content of impurity having aromatic ring in molded body: 149 ppm Detected main impurities each having aromatic ring: diphenyl sulfone, 4,4'-difluorobenzophenone, 4-phenoxybenzaldehyde, bis(4-phenoxyphenyl)methanone, and 2,2-diphenyl-1,3-benzodioxole
(3) Lightness of molded body: L*=78.9
(4) Result of appearance evaluation of molded body: D Comparative Example 5

As a raw material for a dental resin composite material, polyetheretherketone resin powder (150P, Victrex plc, average particle diameter: 1,500 μm, melting point: 343° C., glass transition temperature: 143° C., initial content of impurity having aromatic ring: 544 ppm) was used as it was without heat treatment. The L* value of the polyetheretherketone resin powder (without heat treatment) serving as an indicator of lightness was L*=76.3.

A molded body of a dental resin composite material was obtained by the same method as that of Comparative Example 1 except that 60 parts by mass of the polyetheretherketone resin powder (without heat treatment) was used. The results of the various measurements and evaluation are shown below.
(1) Content of acetone-soluble component in acetone extract solution of molded body: 10 ppm
(2) Content of impurity having aromatic ring in molded body: 326 ppm Detected main impurities each having aromatic ring: diphenyl sulfone, 4,4'-difluorobenzophenone, 4-phenoxybenzaldehyde, bis(4-phenoxyphenyl)methanone, and 2,2-diphenyl-1,3-benzodioxole
(3) Lightness of molded body: L*=77.5
(4) Result of appearance evaluation of molded body: D

The invention claimed is:

1. A method of producing a dental resin composite material, comprising:
a step of heating polyaryletherketone resin powder containing an impurity having an aromatic ring in a heat treatment apparatus to form a polyaryletherketone resin containing 150 ppm or less of the impurity having the aromatic ring, wherein a heating temperature is in a range of a glass transition temperature of the polyaryletherketone resin powder or more to less than a melting point of the polyaryletherketone resin powder, and an internal gas in the heat treatment apparatus is replaced with an external gas existing outside of the heat treatment apparatus while the heating is performed; and
a step of mixing 100 parts by mass of the polyaryletherketone resin containing 150 ppm or less of the impurity having the aromatic ring and 10 parts by mass to 300 parts by mass of inorganic particles in a molten state.

2. The method of producing the dental resin composite material according to claim 1,
wherein, when the heating is performed, a volatile component containing the impurity having the aromatic ring is generated from the heating of the polyaryletherketone resin powder in the heat treatment apparatus, and when the heating is performed, the internal gas having the volatile component is replaced with the external gas so as to prevent the volatile component from adhering to the polyaryletherketone resin powder heated in the heat treatment apparatus.

3. The method of producing the dental resin composite material according to claim 1,
wherein an average particle diameter of the polyaryletherketone resin powder is in a range of 150 μm to 2,000 μm.

4. The method of producing the dental resin composite material according to claim 1,
wherein the internal gas contains an inert gas.

5. The method of producing the dental resin composite material according to claim 1,
wherein the heat treatment apparatus has an absorption filter through which the internal gas passes.

6. The method of producing the dental resin composite material according to claim 1,
wherein the internal gas is continuously or intermittently replaced with the external gas while the heating is performed.

* * * * *